United States Patent [19]

Drent

[11] Patent Number: 4,777,261
[45] Date of Patent: Oct. 11, 1988

[54] PREPARATION OF 2-BENZOXAZOLONES
[75] Inventor: Eit Drent, Amsterdam, Netherlands
[73] Assignee: Shell Oil Company, Houston, Tex.
[21] Appl. No.: 59,083
[22] Filed: Jun. 8, 1987
[30] Foreign Application Priority Data Jul. 30, 1986 [GB] United Kingdom ............... 8618573

[51] Int. Cl.[4] .......................................... C07D 263/58
[52] U.S. Cl. .................................................. 548/221
[58] Field of Search ........................................ 548/221
[56] References Cited

U.S. PATENT DOCUMENTS

| | | | |
|---|---|---|---|
| 3,448,140 | 6/1969 | Gamlen et al. | 260/471 |
| 3,657,265 | 4/1972 | Kober | 548/221 |
| 4,454,322 | 6/1984 | Kervennal et al. | 548/221 |
| 4,558,136 | 12/1985 | White | 548/221 |

Primary Examiner—Nicholas S. Rizzo
Assistant Examiner—Mark W. Noel

[57] ABSTRACT

Preparation of a 2-benzoxazolone by reacting an ortho-nitrophenol with carbon monoxide in the presence of a catalytic system comprising
(a) palladium and/or a palladium compound
(b) a ligand having the formula III

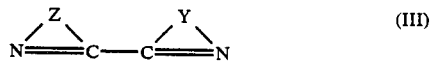

in which Z and Y are the same or different bridging groups each of which has 3 or 4 atoms in the bridge, of which atoms at least two are carbon atoms and which groups Z and Y may be bound to each other by means of a connection other than that already formed by the carbon atoms shown in formula III and
(c) an anion of an acid having a pK of less than 2, except of a hydrohalogenic acid.

13 Claims, No Drawings

PREPARATION OF 2-BENZOXAZOLONES

FIELD OF THE INVENTION

The invention relates to a process for the preparation of 2-benzoxazolones and to 2-benzoxazolones prepared by means of such process.

BACKGROUND OF THE INVENTION

It is known from U.S. Pat. No. 4,454,322 to prepare 2-benzoxazolone or substituted 2-benzoxazolones by reaction of ortho-nitrophenol or a substituted ortho-nitrophenol with carbon monoxide in the presence of a palladium compound, a transition metal and a hetero-aromatic base such as pyridine or quinoline. The catalytic system works only at rather high pressures and temperatures, e.g. at 200° C. and between 150 and 350 bar.

It has now been found that with specific palladium catalyst compositions excellent yields can be obtained under rather mild reaction conditions.

SUMMARY OF THE INVENTION

Accordingly, the present invention provides a process for the preparation of a 2-benzoxazolone, which comprises reacting the corresponding ortho-nitrophenol with carbon monoxide in the presence of a catalytic system comprising
(a) palladium and/or a palladium compound
(b) a ligand having the formula III

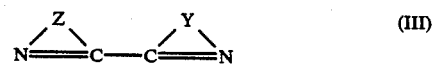

in which Z and Y are the same or different bridging groups each of which has 3 or 4 atoms in the bridge, of which atoms at least two are carbon atoms and which groups Z and Y may be bound to each other by means of a connection other than that already formed by the carbon atoms shown in formula III and
(c) an anion of an acid having a pK of less than 2, except of a hydrohalogenic acid.

The anion forms (is derived from) either part of the acid or a part of a salt of the elements Cu, Fe, V, Cr, Zn, Sn, U and the like.

The process according to the invention is carried out in the presence of palladium or a palladium compound. Palladium can be used as metal, deposited on an inert carrier, such as carbon or alumina, or in the form of palladium compounds, especially palladium salts and equivalent kinds of materials. Excellent results are obtained when the palladium compound is soluble in the reaction mixture.

Examples of palladium salts include palladium chloride, palladium bromide, palladium iodide, sodium tetrachloropalladate, potassium tetrachloropalladate, potassium tetraiodopallate, palladium carboxylates, such as palladium acetate, palladium propionate, palladium isobutyrate, palladium acetylacetonate and equivalent kinds of palladium salts. Preference is given to the use of palladium salts of organic acids, in particular of an alkanoic acid having not more than 12 carbon atoms per molecule. Most preferred is palladium diacetate.

The bridging groups Z and Y in the formula of the ligand are connected with each other via the two carbon atoms as shown. Apart from this connection there may exist a second connection between the bridging groups, as is the case in 1,10-phenanthroline (also called 1,10-diazaphenanthrene) and derivatives thereof. Any atoms in the bridging groups Z and Y other than carbon atoms are preferably nitrogen atoms. Furthermore, Z and Y are preferably the same.

Examples of suitable bidentate ligands of formula III are 2,2'-bipyridyl and derivatives thereof, for example 4,4'-dimethyl-2,2'-bipyridyl, 4,4'-dichloro-2,2'-bipyridyl, 4,4'-dimethoxy-2,2'-bipyridyl, 4,4'-dicarboxy-2,2'-bipyridyl, 2,2'-biquinolyl and equivalent kinds of bidentate ligands.

Other examples of suitable bidentate ligands of formula III are 1,10-phenanthroline and derivatives thereof, for example 5-chlorophenanthroline, 4,7-diphenylphenanthroline, 4,7-dimethylphenanthroline, 2,9-dichlorophenanthroline, 1,10-phenanthroline-5-sulphonic acid, 4,7-diphenyl-1,10-phenanthroline-disulphonic acids and the like.

Further examples of suitable bidentate ligands are 2-(2-pyridyl)benzimidazole, 3-(2-pyridyl)-5,6-diphenyl-1,2,4-triazine, the monosodium salt of 3-(2-pyridyl)-5,6-diphenyl-1,2,4-triazine-p,p'-disulphonic acid and the like.

Preferred ligands are 2,2'-bipyridyl or a derivative thereof or 1,10-phenanthroline or a derivative thereof. Particularly preferred is 1,10-phenanthroline.

The third component of the catalytic system is one in which the anion forms either part of an acid or a part of a salt of the acid with a metal of the group consisting of copper, iron, vanadium, chromium, zinc, tin, uranium and cerium and equivalent kinds of materials. More preferred are copper, iron, vanadium, chromium and uranium. The anion forms part of an acid having a pK of less than 2, except the anion of hydrohalognic acids. Preferred are the anions of the strong acids $H_2SO_4$, $HBF_4$, p-toluene sulphonic acid or alkyl-substituted derivatives of the latter or $HClO_4$. Other suitable acids are for example benzene sulphonic acid, naphthalene sulphonic acid, 2,4,5-trichlorobenzene sulphonic acid, or corresponding bromo- and fluoro-derivatives and the like.

Other examples of acids are those, that can be formed, by interaction of a Lewis acid, such as $BF_3$, $AsF_5$, $SbF_5$, $PF_{5k}$, $TaF_5$ or $NbF_5$ with a Broensted acid, such as a hydrohalogenic acid, e.g. HF, fluorosulphonic acid, phosphoric acid or sulphuric acid. Specific examples are $H_2SiF_6$, $HBF_4$, $HPF_6$ and $HSbF_6$ and the like. Examples of sulphonic acids are fluorosulphonic acid, trifluoromethylsulphonic acid, chlorosulphonic acid and the like.

As specific examples of the compounds falling under (c) may be mentioned copper(1) tosylate, copper(2) tosylate, copper(2) chlorate, iron(2) chlorate, copper(1) fluoroborate, tin(4) sulphate, uranium(4) sulphate and the like.

The basis reaction equation may be written as follows:

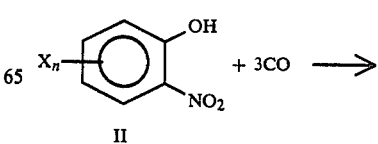

II

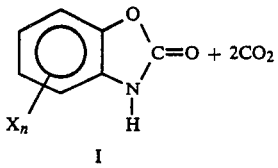

A suitable starting material is ortho-nitrophenol or a substituted derivative thereof, in which one or more places in the six-ring nucleus have been substituted with inert groups or atoms (inert under the reaction circumstances). Such materials are conventionally known in the art and include compounds of the formula II

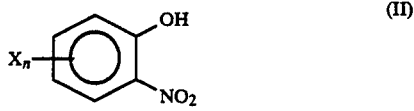

wherein each X is a halogen atom, an alkyl group of from one to ten carbon atoms or a group OR in which R is an alkyl group of from one to ten carbon atoms, a cyano group or a trifluoromethyl group and n is 0 to 4 and equivalent kinds of starting materials.

The product 2-benzoxazolones are conventional chemicals known in the art and include compounds of the formula I

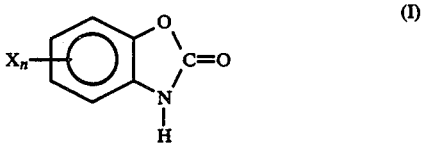

wherein each X is a halogen atom, an alkyl group of from one to ten carbon atoms or a group OR in which R is an alkyl group of from one to ten carbon atoms, a cyano group or a trifluoromethyl group, and n is from 0 to 4 and equivalent kinds of products.

For example, each X may be a halogen atom, preferably chlorine, an alkyl group having from one to ten carbon atoms, preferably having from 1 to 4 carbon atoms, or X may be a group OR, wherein R is alkyl having from one to ten carbon atoms, preferably from one to four carbon atoms. X may also be a cyano group or a $CF_3$-group and n is preferably 0 or 1.

The amount of palladium or palladium compound to be used in the process according to the invention, is conveniently between 0.001 %w, and 10 %w, in particular between 0.01 %w and 2 %w, calculated on the amount of ortho-nitrophenol. Amounts between 0.1 %w and 0.5 %w are most preferred.

The ligand is generally present in such an amount that the mol ratio of ligand:palladium (compound) is between 20 and 0.5.

The amount of acid or salt under (c) may range between 0.1 and 100 mol per gram atom of palladium.

The process according to the invention may be carried out conveniently at temperatures in the range of from 75° C. to 175° C., although higher temperatures are not excluded. The reaction is normally carried out at a pressure in the range of from 10 to 100 bar, although higher pressures are not excluded.

The process according to the present invention is suitably carried out in the presence of an aprotic solvent. Examples of suitable solvents are hydrocarbons, such as hexane, cyclohexane, octane, benzene, toluene, o-xylene, m-xylene, p-xylene, ethylbenzene, cumene, halogenated hydrocarbons, such as chloroform, 1,2-dichloroethane, perfluoroalkanes, chlorobenzene and the three dichlorobenzenes; ethers, such as diethyl ether, tetrahydrofuran, 3,6-dioxaoctane, methyl tert.-butyl ether, dioxane, anisole, 2,5,8-trioxanonane, diphenyl ether, diisopropyl ether and diglyme; N,N-dialkyl substituted amides, such as N,N-dimethylformamide and N-methylpyrrolidone; sulphones such as diisopropyl sulphone and tetrahydrothiophene 1,1-dioxide (also referred to as "sulfolane"); esters, such as methyl benzoate and ethyl acetate, and the like.

The process according to the present invention can be carried out batchwise, semi-continuously or continuously. The reaction time is, of course, related to the temperature and pressure adopted. In general reaction times between 1 and 20 hours are adequate.

The 2-benzoxazolones produced according to the process of the present invention can be used as starting materials for known agrochemicals, dyes, pharmaceuticals or polyurethanes, or may be converted into the corresponding isocyanates by conventional methods known in the art, e.g. by heating the appropriate 2-benzoxazolone.

EXAMPLES

The invention is illustrated by the following examples which should not be regarded as limiting the invention in any way.

EXAMPLE 1

A 300 ml autoclave (Hastelloy C) was charged with orthonitrophenol (10 ml), diglyme (50 ml), palladium diacetate (0.1 mmol), 1,10 phenanthroline (5 mmol) and copper(2) tosylate (0.5 mmol), The autoclave was then pressurized with carbon monoxide. The temperature was raised to 145° C., while the pressure was 75 bar. The reaction mixture was kept at this temperature during 4 hours. The reaction mixture was allowed to cool and was analyzed thereafter by gas-liquid chromatography. The yield of 2-benzoxazolone was 100% (conversion was 100% and selectivity was 100%).

EXAMPLE 2

Example 1 was repeated, except that instead of copper(2) tosylate the corresponding acid (para-toluenesulphonic acid) was used.

The conversion was 66%, with a selectivity to 2-benzoxazolone of 100%.

EXAMPLE 3

(comparative)

The experiment in example 1 was repeated, except that instead of copper(2) tosylate the same molar quantity of $Cu_3(PO_4)_2$ was used. 2-benzoxazolone was not found. (Phosphoric acid has a pKa of 2,12.)

What is claimed is:

1. A process for the preparation of a 2-benzoxazolone which comprises reacting the corresponding ortho-nitrophenol with carbon monoxide in the presence of a catalytic system comprising
    (a) palladium and/or a palladium compound
    (b) a ligand having the formula III

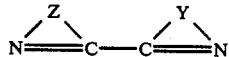

in which Z and Y are the same or different bridging groups each of which has 3 to 4 atoms in the bridge, of which atoms at least two are carbon atoms and which groups Z and Y may be bound to each other by means of a connection other than that already formed by the carbon atoms shown in formula III to form a 1,10-phenanthroline ligand and (c) an anion of an acid having a pK of less than 2, except of a hydrohalogenic acid wherein the reaction is carried out at a temperature in the range of from 75 to about 175° C. and at a pressure in the range of from 10 to about 100 bar.

2. A process according to claim 1 wherein the nitrophenol has the formula II

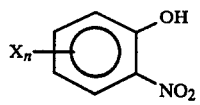

wherein each X is a halogen atom, an alkyl group of from one of ten carbon atoms or a group OR in which R is an alkyl group of from one to ten carbon atoms, a cyano group or a trifluoromethyl group, and n is from 0 to 4.

3. A process according to claim 1 in which the anion is derived from $H_2SO_4$, $HBF_4$, p-toluene sulphonic acid or alkyl substituted derivative of the latter, or $HClO_4$.

4. A process according to claim 3 in which either the acid or a salt of the acid with Cu, Fe, C, Cr, Zn, Sn, U or Ce is used.

5. A process according to claim 3 in which copper(2) tosylate, copper(2) chlorate, iron(2) chloride, copper(2) fluoroborate, zinc fluoroborate, tin(4) sulphate or uranium(4) sulphate is used.

6. A process according to claim 1 in which the ligand is 1,10-phenanthroline or a derivative thereof selected from 5-chlorophenanthroline, 4,7-diphenylphenanthroline, 4,7-dimethylphenanthroline, 2,9-dichlorophenanthroline, 1,10-phenanthroline-5-sulphonic acid or 4,7-diphenyl-1,10-phenanthroline-disulphonic acid.

7. A process according to claim 1 in which the palladium catalyst is a homogeneous catalyst.

8. A process according to claim 7 in which the catalyst is a palladium salt.

9. A process according to claim 8 in which the catalyst is palladium diacetate.

10. A process according to claim 1 wherein the 2-benzoxazolone has the formula I

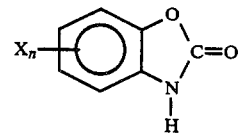

wherein each X is a halogen atom, an alkyl group of from one to ten carbon atoms or a group OR in which R is an alkyl group of from one to ten carbon atoms, a cyano group or a trifluoromethyl group and n is 0 to 4 and the palladium catalyst is a homogeneous catalyst.

11. A process according to claim 10 in which the anion is derived from $H_2SO_4$, $HBF_4$, p-toluene sulphonic acid or alkyl substituted derivative of the latter, or $HClO_4$.

12. A process according to claim 11 in which the palladium catalyst is a palladium salt, the ligand is 1,10-phenanthroline or a derivative thereof and the anion is derived from either the acid or a salt of the acid with Cu, Fe, V, Cr, Zn, Sn, U or Ce.

13. A process according to claim 12 wherein the catalyst is palladium diacetate and the anion is derived from copper(2) tosylate, copper(2) chlorate, iron(2) chlorate, copper(2) fluoroborate, zinc fluoroborate, tin(4) sulphate or uranium(4) sulphate.

* * * * *